United States Patent
Luo et al.

(10) Patent No.: US 9,927,727 B2
(45) Date of Patent: Mar. 27, 2018

(54) METHOD TO MAKE A PHOTOCONDUCTOR HAVING AN OVERCOAT WITH TETRAFUNCTIONAL RADICAL POLYMERIZABLE CHARGE TRANSPORT MOLECULE

(71) Applicant: LEXMARK INTERNATIONAL, INC., Lexington, KY (US)

(72) Inventors: Weimei Luo, Louisville, CO (US); David Glenn Black, Broomfield, CO (US); Mark Thomas Bellino, Loveland, CO (US)

(73) Assignee: LEXMARK INTERNATIONAL, INC., Lexington, KY (US)

( * ) Notice: Subject to any disclaimer, the term of this patent is extended or adjusted under 35 U.S.C. 154(b) by 29 days.

(21) Appl. No.: 14/983,928

(22) Filed: Dec. 30, 2015

(65) Prior Publication Data
US 2017/0192368 A1  Jul. 6, 2017

(51) Int. Cl.
G03G 5/05 (2006.01)
G03G 7/00 (2006.01)
G03G 5/147 (2006.01)
G03G 5/06 (2006.01)

(52) U.S. Cl.
CPC ......... *G03G 5/0525* (2013.01); *G03G 5/0614* (2013.01); *G03G 5/14734* (2013.01); *G03G 7/0006* (2013.01)

(58) Field of Classification Search
CPC ............. G03G 5/14734; G03G 5/0614; G03G 7/0006; G03G 5/0525
See application file for complete search history.

(56) References Cited

U.S. PATENT DOCUMENTS

| | | | | |
|---|---|---|---|---|
| 6,416,915 | B1 * | 7/2002 | Kikuchi | G03G 5/0614 430/58.45 |
| 9,034,543 | B2 * | 5/2015 | Iwadate | G03G 5/0618 430/58.7 |
| 2011/0129768 | A1 * | 6/2011 | Nonaka | G03G 5/0614 430/56 |
| 2014/0186758 | A1 * | 7/2014 | Bellino | G03G 5/14786 430/66 |
| 2015/0185628 | A1 * | 7/2015 | Black | G03G 5/0614 430/58.65 |

FOREIGN PATENT DOCUMENTS

JP   2015049314 A  *  3/2015

* cited by examiner

*Primary Examiner* — Christopher D Rodee (57) ABSTRACT

A method to make an improved organic photoconductor drum of an electrophotographic image forming device is provided. The improved organic photoconductor drum is prepared using a curable composition including a charge transport molecule containing four radical polymerizable functional groups of the general structure exemplified below:

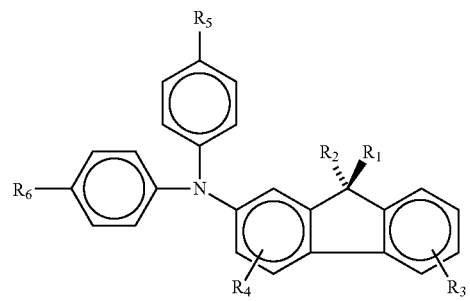

where $R_1$ and $R_2$ contain a spacer group and a radical polymerizable functional group, $R_3$ and $R_4$ are selected from the group consisting of a radical polymerizable functional group, a non-radical polymerizable functional group, and one each of a radical polymerizable functional group and a non-radial polymerizable functional group, and $R_5$ and $R_6$ contain a spacer group and a radical polymerizable functional group.

7 Claims, 2 Drawing Sheets

METHOD TO MAKE A PHOTOCONDUCTOR HAVING AN OVERCOAT WITH TETRAFUNCTIONAL RADICAL POLYMERIZABLE CHARGE TRANSPORT MOLECULE

CROSS REFERENCES TO RELATED APPLICATIONS

None.

BACKGROUND

1. Field of the Disclosure

The present disclosure relates generally to electrophotographic image forming devices, and more particularly to a method to make an organic photoconductor drum having and overcoat with a tetrafunctional radical polymerizable charge transport molecule.

2. Description of the Related Art

Organic photoconductor drums have generally replaced inorganic photoconductor drums in electrophotographic image forming device including copiers, facsimiles and laser printers due to their performance and advantages. These advantages include improved optical properties such as having a wide range of light absorbing wavelengths, improved electrical properties such as having high sensitivity and stable chargeability, availability of materials, good manufacturability, low cost, and low toxicity.

While the performance and advantages offered by organic photoconductor drums are significant, inorganic photoconductor drums offer much higher durability. Inorganic photoconductor drums (e.g., amorphous silicon photoconductor drums) are ceramic-based, thus being extremely hard and abrasion resistant. The surface of organic photoconductor drums is typically comprised of a low molecular weight charge transport material, and an inert polymeric binder. Therefore, the failure mechanism for organic photoconductor drums typically arises from mechanical abrasion of the surface layer due to repeated use. Abrasion of photoconductor drum surface may arise from its interaction with print media (e.g. paper), paper dust, or other components of the electrophotographic image forming device.

The abrasion of photoconductor drum surface degrades its electrical properties, such as sensitivity and charging properties. Electrical degradation results in poor image quality, such as lower optical density, and background fouling. When a photoconductor drum is locally abraded, images often have black toner bands due to the inability to hold charge in the thinner regions. This black banding often marks the end of the life of the photoconductor drum.

Increasing the life of the photoconductor drum will allow the photoconductor drum to become a permanent part of the electrophotographic image forming device. In other words, the photoconductor drum will no longer be a replaceable unit nor be viewed as a consumable. Photoconductor drums with a life-of-the-printer will allow the printer to operate with lower cost-per-page, more stable image quality, and less waste.

To achieve a long life photoconductor drum, especially with organic photoconductor drum, a protective overcoat layer may be coated onto the surface of the photoconductor drum. An overcoat layer formed from a crosslinkable silicon material has been known to improve life of the photoconductor drums used for color printers. However, such overcoat layer does not have the robustness for edge wear of photoconductor drums used in mono printers. A photoreceptor overcoat comprising a UV crosslinked layer of hexacoordinate urethane acrylate and UV crosslinkable charge transport molecule is disclosed in U.S. Pat. No. 8,940,466 entitled "PHOTOCONDUCTOR OVERCOATS COMPRISING RADICAL POLYMERIZABLE CHARGE TRANSPORT MOLECULES AND HEXA FUNCTIONAL URETHANE ACRYLATES", which is assigned to the assignee of the present application and is incorporated by reference herein in its entirety. While this overcoat system improves paper edge wear versus crosslinkable silicon materials, a still greater improvement is needed and desired.

While a robust overcoat layer improves the life of photoconductor drums, a suitable overcoat layer is required that does not significantly alter the electrophotographic properties of the photoconductor drum. If the overcoat layer is too electrically insulating, the photoconductor drum will not discharge and will result in a poor latent image. On the other hand, if the overcoat layer is too electrically conducting, then the electrostatic latent image will spread resulting in a blurred image. Thus, a protective overcoat layer that improves life of the photoconductor drum must also allow charge migration to the photoconductor surface for development of the latent image with toner.

SUMMARY

The present disclosure provides an overcoat layer for an organic photoconductor drum of an electrophotographic image forming device. The overcoat layer is prepared from a curable composition including a charge transport molecule containing four radical polymerizable functional groups of the general structure exemplified below:

where $R_1$ and $R_2$ contain a spacer group and a radical polymerizable group, $R_3$ and $R_4$ contain either a radical polymerizable group, a non-radical polymerizable group, or one each of a radical polymerizable group and a non-radial polymerizable group, and $R_5$ and $R_6$ contain a spacer group and a radical polymerizable group. The curable composition also contains at least one curing agent.

Also disclosed is a photoconductor drum comprising a support element, a charge generation layer disposed over the support element, a charge transport layer disposed over the charge generation layer, and an overcoat layer disposed over the charge transport layer comprising a curable composition including a charge transport molecule containing four radical polymerizable functional groups as exemplified below:

where $R_1$ and $R_2$ contain a spacer group and a radical polymerizable functional group, $R_3$ and $R_4$ contain either a radical polymerizable functional group, a non-radical polymerizable functional group, or one each of a radical polymerizable functional group and a non-radial polymerizable functional group, and $R_5$ and $R_6$ contain a spacer group and a radical polymerizable functional group. The curable composition also contains at least one curing agent.

BRIEF DESCRIPTION OF THE DRAWINGS

The accompanying drawings incorporated in and forming a part of the specification, illustrate several aspects of the present disclosure, and together with the description serve to explain the principles of the present disclosure.

DETAILED DESCRIPTION

It is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the terms "a" and "an" herein do not denote a limitation of quantity, but rather denote the presence of at least one of the referenced item.

Figure 1:
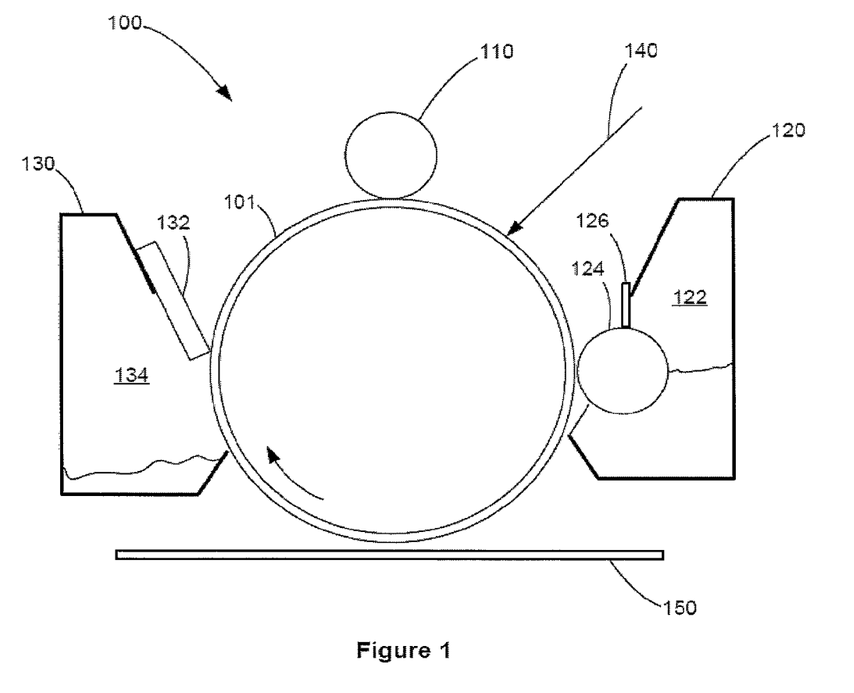
FIG. 1 is a schematic view of an electrophotographic image forming device.

FIG. 1 illustrates a schematic representation of an example electrophotographic image forming device 100. Image forming device 100 includes a photoconductor drum 101, a charge roll 110, a developer unit 120, and a cleaner unit 130. The electrophotographic printing process is well known in the art and, therefore, is described briefly herein. During a print operation, charge roll 110 charges the surface of photoconductor drum 101. The charged surface of photoconductor drum 101 is then selectively exposed to a laser light source 140 to form an electrostatic latent image on photoconductor drum 101 corresponding to the image being printed. Charged toner from developer unit 120 is picked up by the latent image on photoconductor drum 101 creating a toned image.

Developer unit 120 includes a toner sump 122 having toner particles stored therein and a developer roll 124 that supplies toner from toner sump 122 to photoconductor drum 101. Developer roll 124 is electrically charged and electrostatically attracts the toner particles from toner sump 122. A doctor blade 126 disposed along developer roll 124 provides a substantially uniform layer of toner on developer roll 124 for subsequent transfer to photoconductor drum 101. As developer roll 124 and photoconductor drum 101 rotate, toner particles are electrostatically transferred from developer roll 124 to the latent image on photoconductor drum 101 forming a toned image on the surface of photoconductor drum 101. In one embodiment, developer roll 124 and photoconductor drum 101 rotate in the same rotational direction such that their adjacent surfaces move in opposite directions to facilitate the transfer of toner from developer roll 124 to photoconductor drum 101. A toner adder roll (not shown) may also be provided to supply toner from toner sump 122 to developer roll 124. Further, one or more agitators (not shown) may be provided in toner sump 122 to distribute the toner therein and to break up any clumped toner.

The toned image is then transferred from photoconductor drum 101 to print media 150 (e.g., paper) either directly by photoconductor drum 101 or indirectly by an intermediate transfer member. A fusing unit (not shown) fuses the toner to print media 150. A cleaning blade 132 (or cleaning roll) of cleaner unit 130 removes any residual toner adhering to photoconductor drum 101 after the toner is transferred to print media 150. Waste toner from cleaning blade 132 is held in a waste toner sump 134 in cleaning unit 130. The cleaned surface of photoconductor drum 101 is then ready to be charged again and exposed to laser light source 140 to continue the printing cycle.

The components of image forming device 100 are replaceable as desired. For example, in one embodiment, developer unit 120 is housed in a replaceable unit with photoconductor drum 101, cleaner unit 130 and the main toner supply of image forming device 100. In another embodiment, developer unit 120 is provided with photoconductor drum 101 and cleaner unit 130 in a first replaceable unit while the main toner supply of image forming device 100 is housed in a second replaceable unit. In another embodiment, developer unit 120 is provided with the main toner supply of image forming device 100 in a first replaceable unit and photoconductor drum 101 and cleaner unit 130 are provided in a second replaceable unit. Further, any other combination of replaceable units may be used as desired. In some example embodiment, the photoconductor drum 101 may not be replaced and is a permanent component of the image forming device 100.

Figure 2:
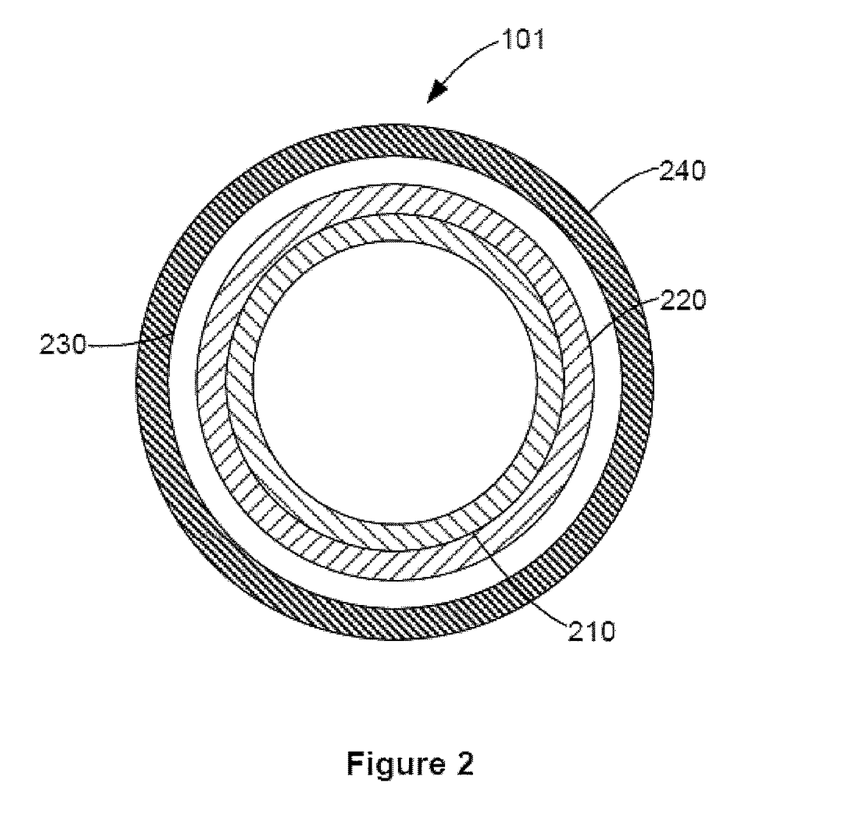
FIG. 2 is a cross-sectional view of a photoconductor drum of the electrophotographic image forming device.

FIG. 2 illustrates an example photoconductor drum 101 in more detail. In this example embodiment, the photoconductor drum 101 is an organic photoconductor drum and includes a support element 210, a charge generation layer 220 disposed over the support element 210, a charge transport layer 230 disposed over the charge generation layer 220, and a protective overcoat layer 240 formed as an outermost layer of the photoconductor drum 101. Additional layers may be included between the support element 210, the charge generation layer 220 and the charge transport layer 230, including adhesive and/or coating layers.

The support element 210 as illustrated in FIG. 2 is generally cylindrical. However the support element 210 may assume other shapes or may be formed into a belt. In one example embodiment, the support element 210 may be formed from a conductive material, such as aluminum, iron, copper, gold, silver, etc. as well as alloys thereof. The surfaces of the support element 210 may be treated, such as by anodizing and/or sealing. In some example embodiment, the support element 210 may be formed from a polymeric material and coated with a conductive coating.

The charge generation layer 220 is designed for the photogeneration of charge carriers. The charge generation layer 220 may include a binder and a charge generation compound. The charge generation compound may be understood as any compound that may generate a charge carrier in response to light. In one example embodiment, the charge generation compound may comprise a pigment being dispersed evenly in one or more types of binders.

The charge transport layer 230 is designed to transport the generated charges. The charge transport layer 230 may include a binder and a charge transport compound. The charge transport compound may be understood as any compound that may contribute to surface charge retention in the dark and to charge transport under light exposure. In one example embodiment, the charge transport compounds may include organic materials capable of accepting and transporting charges.

In an example embodiment, the charge generation layer 220 and the charge transport layer 230 are configured to combine in a single layer. In such configuration, the charge generation compound and charge transport compound are mixed in a single layer. The overcoat layer 240 is designed to protect the photoconductor drum 101 from wear and abrasion without altering the electrophotographic properties, thus extending the service life of the photoconductor drum 101. The overcoat layer 240 has a thickness of about 0.1 μm to about 10 μm. Specifically, the overcoat layer 240 has a thickness of about 1 μm to about 6 μm, and more specifically a thickness of about 3 μm to about 5 μm. The thickness of the overcoat layer 240 is kept at a range that will not provide adverse effect to the electrophotographic properties of the photoconductor drum 101.

The overcoat layer comprises the cured, or substantially crosslinked, product of a crosslinkable hole transporting material containing four radical polymerizable functional groups and at least one curing agent. The overcoat layer may further comprise an optional non-crosslinkable additive.

The terms "crosslinkable" and "radical polymerizable," and derivatives thereof, may be used interchangeably. "Cured" herein refers to, for example, a state in which the crosslinkable charge transport molecule containing four radical polymerizable groups and the at least one curing agent in the coating solution firm a crosslinked or substantially crosslinked product. "Substantially crosslinked" in embodiments refers to, for example, a state in which about 60% to 100% of the charge transport compounds in the overcoat composition, for example about 70% to 100% or about 80% to 100%, are covalently bound in the composition. Curing in the present invention occurs by exposing the curable composition to ionizing electromagnetic radiation of suitable wavelength or by exposure to an electron beam. Crosslinking of the reactive components occurs following application of the overcoat coating composition to the photoconductor.

The following discussion seeks to define the crosslinkable charge transport molecule containing four radical polymerizable groups by describing the fluorene and diphenylamine fragments separately. The crosslinkable charge transport compound of the present invention comprises a nitrogen atom bonded directly to one fluorene group and two phenyl groups. Fluorene has the following molecular structure:

The fluorene moiety may be fluorene or a fluorene derivative. Fluorene derivatives have the above core structure, with different groups bonded to the core structure. By convention, the carbon atoms are numbered 1-9. The crosslinkable compound of the present invention is substituted in the 9-position with two functional groups comprising a radical polymerizable group. The substituted fluorene group thus has the molecular structure show below:

The substituent's $R_1$ and $R_2$ are functional groups containing a spacer group and a radical polymerizable group. The spacer group separates the 9-position of the fluorene ring from the radical polymerizable functional group. The bonds are represented with $R_1$ coming out of the page, and $R_2$ going behind the page. In other words, $R_1$ and $R_2$ are oriented perpendicular to the plane of the fluorene group. In principle, $R_1$ and $R_2$ may be the same or different functional group containing a spacer group and a radical polymerizable group. In a practical sense, $R_1$ and $R_2$ are the same functional group containing a spacer group and a radical polymerizable group. The radical polymerizable group is separated from the 9-position of the fluorene ring by a spacer group of at least one carbon. In principle, this spacer group may be any branched or unbranched saturated hydrocarbon group having the general formula $C_nH_{2n}$, wherein n is, for example, a number from 1 to about 100 or more, such as methyl, ethyl, n-propyl, isopropyl, n-butyl, isobutyl, tert-butyl, octyl, decyl, tetradecyl, hexadecyl, eicosyl, tetracosyl, and the like. As used herein, the term spacer group is defined as a $C_nH_{2n}$ group. In a practical sense, the spacer group of $R_1$ and $R_2$ is an unbranched alkyl group containing between 1 and about 12 carbon atoms. More specifically, the alkyl group is an unbranched alkyl group containing between 1 and 6 carbon atoms. In an example embodiment, the spacer group of $R_1$ and $R_2$ is an ethyl group.

The radical polymerizable group of $R_1$ and $R_2$ is any functional group that is capable of undergoing radical polymerization (crosslinking) upon absorption of electromagnetic radiation, or by exposure to an electron beam. The radical polymerizable group may be selected from the group consisting of acrylate group, methacrylate group, styrenic group, allylic group, vinylic group, glycidyl ether group and epoxy group. In an example embodiment, the radical polymerizable group is an acrylate group. The substituted fluorene group thus has the molecular structure shown below:

R₃ and R₄ may be the same or different from R₁ and R₂. R₃ and R₄ may both contain a radical polymerizable functional group, both contain a non-radical polymerizable group, or contain one each of a radical polymerizable group and a non-radical polymerizable group. The radical polymerizable groups may be selected from the group consisting of acrylate group, methacrylate group, styrenic group, allylic group, vinylic group, glycidyl ether group and epoxy group. The non-radical polymerizable groups may be any group without limitation, including H, an alkyl group, an alkoxyl group, an aryl group, an aryl alkyl groups, an alcohol group, an alkyl alcohol group and the like. R₃ and R₄ may be covalently bonded to any of the 1-8 positions of the fluorene group. In an example embodiment, R₃ and R₄ are hydrogen atoms. The substituted fluorene, group thus has the molecular structure shown below:

The crosslinkable compound of the present invention also comprises two phenyl groups. The phenyl groups further contain substituents R₅ and R₆. The substituted phenyl groups are exemplified for clarity as the diphenylamine fragment shown below:

The substituents R₅ and R₆ comprise a spacing group and a radical polymerizable group. The spacer group separates the phenyl group from the radical polymerizable functional group. The bonds are represented with the bonds for R₅ and R₆ in the same plane as the phenyl group. In principle, R₅ and R₆ may be the same or different functional group containing a spacer group and a radical polymerizable group. In a practical sense, R₅ and R₆ are the same functional group containing a spacer group and a radical polymerizable group. The radical polymerizable group is separated from the phenyl group by a spacer group of at least one carbon. In principle, this spacer group may be any branched or unbranched saturated hydrocarbon group having the general formula $C_nH_{2n}$, wherein n is, for example, a number from 1 to about 100 or more, such as methyl, ethyl, n-propyl, isopropyl, n-butyl, isobutyl, tert-butyl, octyl, decyl, tetradecyl, hexadecyl, eicosyl, tetracosyl, and the like. In a practical sense, the spacer group of R₅ and R₆ is an unbranched alkyl group containing between 1 and about 12 carbon atoms. More specifically, the alkyl group is an unbranched alkyl group containing between 1 and 6 carbon atoms. In an example embodiment, the spacer group of R₅ and R₆ is an ethyl group.

The radical polymerizable group of R₅ and R₆ are both located in the para position relative to the nitrogen. The inventors have found that this regiochemistry gives a crosslinkable charge transport compound with electrical properties suitable for a photoconductor of the present invention. The radical polymerizable group of R₅ and R₆ is any functional group that is capable of undergoing radical polymerization (crosslinking) upon absorption of electromagnetic radiation, or by exposure to an electron beam. The radical polymerizable group may be selected from the group consisting of acrylate group, methacrylate group, styrenic group, allylic group, vinylic group, glycidyl ether group and epoxy group. In an example embodiment, the radical polymerizable group is an acrylate group. The radical polymerizable group of R₅ and R₆ may be the same or different from the radical polymerizable group of R₁ and R₂. In an example embodiment, the radical polymerizable group is an acrylate group.

Combining the fluorene and diphenylamine fragments gives the crosslinkable charge transport molecule of the present invention with the molecular structure shown below:

The curable composition of the present invention also includes a curing agent. The general purpose of the curing agent is to further improve the abrasion resistance of the overcoat. The curing agent may also improve the adhesion of the cured overcoat to the underlying layer. In one embodiment, the curing agent is a urethane resin containing six radical polymerizable functional groups. The radical polymerizable groups may be selected from the group consisting of acrylate group, methacrylate group, styrenic group, allylic group, vinylic group, glycidyl ether group and epoxy group. In another embodiment, the radical polymerizable group is an acrylate. In an example embodiment, the curing agent is a urethane acrylate containing six acrylate groups of the following structure:

and is commercially available from Cytec Industries under the trade name EBECRYL 8301.

The synthesis of urethane acrylates involves reaction of a diisocyanate with pentaerythritol triacrylate in the presence of a catalyst. In a general sense, the choice of isocyanate and/or hydroxy acrylate plays a large role in determining the mechanical and thermal properties of the radically cured material. Curing of urethane acrylates, such as the material described above, creates a 3-dimensionally crosslinked structure. Increasing the crosslink density of the radically cured material is one way to improve the mechanical and thermal properties of the materials. Urethane resins containing six acrylate groups are preferred curing agents for the present invention since crosslink density increases with the number of radical polymerizable functional groups. High crosslink density is known to improve properties such as abrasion and chemical resistance. The crosslinked 3-dimensional network should be homogeneous throughout the cured material, since this improves mechanical and thermal properties. Homogeneous crosslinking is also important for applications requiring a high degree of optical transparency.

The curable composition comprising a charge transport molecule containing four radical polymerizable functional groups and optional urethane resin containing six radical polymerizable functional groups exemplifies the overcoat layer 240 with excellent abrasion resistance. In an electrophotographic printer, such as a laser printer, an electrostatic image is created by illuminating a portion of the photoconductor surface in an image-wise manner. The wavelength of light used for this illumination is most typically matched to the absorption max of a charge generation material, such as titanylphthalocyanine. Absorption of light results in creation of an electron-hole pair. Under the influence of a strong electrical field, the electron and hole (radical cation) dissociate and migrate in a field-directed manner. Photoconductors operating in a negative charging manner moves holes to the surface and electrons to ground. The holes discharge the photoconductor surface, thus leading to creation of the latent image. Cured overcoats comprising a charge transport molecule containing four radical polymerizable functional groups provides electrical properties that approach those of the underlying charge transport layer 230. Combining a charge transport molecule containing four radical polymerizable functional groups with a urethane resin containing six radical polymerizable groups provides an overcoat 240 with improved abrasion resistance, along with excellent electrical properties for the photoconductor drum 101.

Ultimately this overcoat formulation of the present invention leads to a photoconductor drum having an 'ultra long life', thereby allowing a consumer to successfully print at least 100,000 pages on their printer before they have to go purchase a replacement photoconductor drum.

In one embodiment, the curable composition comprises a combination of a charge transport molecule containing four radical polymerizable functional groups and a curing agent comprising a urethane resin containing six radical polymerizable functional groups. The curable composition includes about 20 to about 80 percent by weight of the charge transport molecule containing four radical polymerizable functional groups, and about 20 to about 80 percent by weight of urethane resin containing six radical polymerizable functional groups. In more particular, the curable composition includes about 40 to about 60 percent by weight of charge transport molecule containing four radical polymerizable functional groups and about 40 to about 60 percent by weight of the urethane resin containing six radical polymerizable functional groups. This combination provides both the charge transporting properties of the charge transport molecule containing four radical crosslinkable functional groups with the abrasion resistance of the urethane resin containing six radical polymerizable functional groups. Additionally, the overcoats of the present invention have (1) excellent adhesion to the photoconductor surface, (2) optical transparency and (3) crack free. Overcoat delamination (poor adhesion) from the photoconductor surface has been noted as a problem in the prior art.

Overcoat layers are typically coated in solvent systems designed to solubilize components of the overcoat formulation, while minimizing dissolution of the underlying photoconductor structure. Dissolution of components comprising the underlying photoconductor results in materials with no radical polymerizable functionality entering the overcoat layer. The result is dramatically lower crosslinking density and lower abrasion resistance since the properties of the overcoat layer are optimized by an uninterrupted 3-dimensional network. Ideally, the overcoat layer is distinct from the underlying photoconductor surface. However, the interface between the overcoat and the photoconductor surface often lacks the chemical interactions required for strong adhesion. The overcoats of the present invention have excellent adhesion to the photoconductor surface throughout the print life of the photoconductor. The overcoat must also be optically transparent. Illumination of the photoconductor in an image-wise manner requires that layers not involved in the charge generation process be transparent to the incident light. Additionally, optical transparency is an indicator of material and crosslink homogeneity within the overcoat structure. The overcoats of the present invention have a high degree of optical transparency throughout the print life of the photoconductor. The overcoat must also be crack free. UV or Electron beam cured films often exhibit cracks as a result of unrelieved internal stress. These cracks will manifest immediately in print, and will dramatically decrease the functional life of the overcoat. The overcoats of the present invention are crack free throughout the print life of the photoconductor.

The curable composition may further include a curing agent comprising a monomer or oligomer having at most five radical polymerizable functional groups. The radical polymerizable functional groups of the monomer or oligomer may be selected from the group consisting of acrylate group, methacrylate group, styrenic group, allylic group, vinylic group, glycidyl ether group, epoxy group, or combinations thereof. Suitable examples of mono-functional monomer or oligomer include, but are not limited to, methyl acrylate, methyl methacrylate, ethyl acrylate, ethyl methacrylate, propyl acrylate, propyl methacrylate, isobornyl acrylate, isobornyl methacrylate, 2-phenoxyethyl acrylate, and lauryl methacrylate.

Suitable examples of di-functional monomer or oligomer include, but are not limited to, diacrylates and dimethacrylates, comprising 1,4-butanediol diacrylate, 1,4-butanediol dimethacrylate, ethylene glycol dimethacrylate, diethylene glycol diacrylate, diethylene glycol dimethacrylate, triethylene glycol diacrylate, triethylene glycol dimethacrylate, 1,3-butylene glycol diacrylate, 1,6-hexanediol diacrylate, 1,6-hexanediol dimethacrylate, 1,12-dodecanediol methacrylate, tripropylene glycol diacrylate, 1,3-butylene glycol dimethacrylate, 1,3-butylene glycol dimethacrylate, cyclohexane dimethanol diacrylate esters, or cyclohexane dimethanol dimethacrylate esters.

Suitable examples of tri-functional monomer or oligomer include, but are not limited to, trimethylolpropane triacrylate, trimethylolpropane trimethacrylate, hydroxypropyl acrylate-modified trimethylolpropane triacrylate, ethylene oxide-modified trimethylolpropane triacrylate, propylene oxide-modified trimethylolpropane triacrylate, and caprolactone-modified trimethylolpropane triacrylate. More specifically, the tri-functional monomer or oligomer includes propoxylated (3) trimethylolpropane triacrylate, ethoxylated (6) trimethylolpropane triacrylate, propoxylated (6) trimethylolpropane triacrylate, and ethoxylated (9) trimethylolpropane triacrylate.

Suitable examples of monomers or oligomers having four radical polymerizable functional groups include, but are not limited to, pentaerythritol tetraacrylate, di-trimethylolpropane tetraacrylate, and ethoxylated pentaerythritol tetraacrylate. Suitable examples of monomers or oligomers having five radical polymerizable functional groups include, but are not limited to, pentaacrylate esters and dipentaerythritol pentaacrylate esters.

The curable composition may further include a non-radical polymerizable additive such as a surfactant at an amount equal to or less than about 10 percent by weight of the curable composition. More specifically, the amount of non-radical polymerizable additive is about 0.1 to about 5 percent by weight of the curable composition. The non-radical polymerizable additive may improve coating uniformity of the curable composition.

The curable composition is prepared by mixing the charge transport molecule containing four radical polymerizable groups and optional curing agent in a solvent. The solvent may include organic solvents such as tetrahydrofuran (THF), toluene, alkanes such as hexane, butanone, cyclohexanone and alcohols. The solvent may include a mixture of two or more organic solvents to solubilize the crosslinkable charge transport compound containing four radical polymerizable functional groups and the urethane resin having six radical polymerizable functional groups.

The curable composition may be coated on the outermost surface of the photoconductor drum 101 through dipping or spraying. If the curable composition is applied through dip coating, an alcohol is used as the solvent to minimize dissolution of the components of the charge transport layer 230. The alcohol solvent includes isopropanol, methanol, ethanol, butanol, or combinations thereof.

The coated curable composition is then exposed a radiation source of sufficient energy to induce formation of free radicals to initiate the crosslinking reaction. The exposed composition is then post-baked to anneal and relieve stresses in the coating. The radiation source of sufficient energy to induce formation of free radicals is either a UV source, or an electron beam source. If a UV source is used to generate free radicals, the curable composition may contain a photoinitiator.

Specific examples of photo initiators for use under UV cure conditions include acetone or ketal photo polymerization initiators such as diethoxyacetophenone, 2,2-dimethoxy-1,2-diphenylethane-1-one, 1-hydroxy-cyclohexylphenyl-ketone, 4-(2-hydroxyethoxy)phenyl-(2-hydroxy-2-propyl)ketone, 2-benzyl-2-dimethylamino-1-(4-molpholinophenyl)butanone-1,2-hydroxy-2-methyl-1-phenylpropane-1-one and 1-phenyl-1,2-propanedion-2-(o-ethoxycarbonyl)oxime; benzoinether photo polymerization initiators such as benzoin, benzoinmethylether, benzoinethylether, benzoinisobutylether and benzoinisopropylether; benzophenone photo polymerization initiators such as benzophenone, 4-hydroxybenzophenone, o-benzoylmethylbenzoate, 2-benzoylnaphthalene, 4-benzoylviphenyl, 4-benzoylphenylether, acrylated benzophenone and 1,4-benzoylbenzene; thioxanthone photo polymerization initiators such as 2-isopropylthioxanthone, 2-chlorothioxanthone, 2,4-dimethylthioxanthone, 2,4-diethylthioxanthone and 2,4-dichlorothioxanthone; phenylglyoxylate photoinitiators such as methylbenzoylformate and other photo polymerization initiators such as ethylanthraquinone, 2,4,6-trimethylbenzoyldiphenylphosphineoxide, 2,4,6-trimethylbenzoyldiphenylethoxyphosphineoxide, bis(2,4,6-trimethylbenzoyl)phenylphosphineoxide, bis(2,4-dimethoxybenzoyl)-2,4,4-trimethylpentylphosphineoxide, methylphenylglyoxyester, 9,10-phenanthrene, acridine compounds, triazine compounds and imidazole compounds. Further, a material having a photo polymerizing effect can be used alone or in combination with the above-mentioned photo polymerization initiators. Specific examples of the materials include triethanolamine, methyldiethanol amine, 4-dimethylaminoethylbenzoate, 4-dimethylaminoisoamylbenzoate, ethyl(2-dimethylamino)benzoate and 4,4-dimethylaminobenzophenone. These polymerization initiators can be used alone or in combination. The loading of photoinitiator is between about 0.5 to about 20 parts by weight and more specifically from about 2 to about 10 parts by weight per 100 parts by weight of the curable composition.

Curing the composition by electron beam does not require the presence of a photoinitiator and thus may result in greater crosslink density. In an example embodiment, the radiation source of sufficient energy to induce formation of free radicals is electron beam.

Preparation of Example Photoconductor Drum

An Example Photoconductor Drum was formed using an aluminum substrate, a charge generation layer coated onto the aluminum substrate, and a charge transport layer coated on top of the charge generation layer.

The charge generation layer was prepared from a dispersion including type IV titanyl phthalocyanine, polyvinylbutyral, poly(methyl-phenyl)siloxane and polyhydroxystyrene at a weight ratio of 45:27.5:24.75:2.75 in a mixture of 2-butanone and cyclohexanone solvents. The polyvinylbutyral is available under the trade name BX-1 by Sekisui Chemical Co., Ltd. The charge generation dispersion was coated onto the aluminum substrate through dip coating and dried at 100° C. for 15 minutes to form the charge generation layer having a thickness of less than 1 µm, specifically a thickness of about 0.2 µm to about 0.3 µm.

The charge transport layer was prepared from a formulation including terphenyl diamine derivatives and polycarbonate at a weight ratio of 50:50 in a mixed solvent of THF and 1,4-dioxane. The charge transport formulation was coated on top of the charge generation layer and cured at 120° C. for 1 hour to form the charge transport layer having a thickness of about 17 µm to about 19 µm as measured by an eddy current tester.

EXAMPLE 1

The inventive overcoat layer of the present invention was prepared from a formulation including EBECRYL 8301 (20 g) and ethanol (80 g) and the crosslinkable charge transport molecule containing four radical polymerizable functional groups (20 g) shown below:

The formulation was coated through dip coating on the outer surface of the Example Photoconductor Drum formed as outlined above. The coated layer was then exposed to an electron beam source at an accelerating voltage of 90 kV, a current of 3 mA, and an exposure time of 1.2 seconds. The electron beam cured photoreceptor was then thermally cured at 120° C. for 60 minutes. The cured layer forms the overcoat layer having a thickness of about 4.3 µm as measured by an eddy current tester.

COMPARATIVE EXAMPLE 1

An overcoat layer was prepared from a formulation including EBECRYL 8301 (20 g) and ethanol (80 g) and a crosslinkable charge transport molecule containing two radical polymerizable functional groups (20 g) shown below:

The formulation was coated through dip coating on the outer surface of the Example Photoconductor Drum formed as outlined above. The coated layer was then exposed to an electron beam source at an accelerating voltage of 90 kV, a current of 3 mA, and an exposure time of 1.2 seconds. The electron beam cured photoreceptor was then thermally cured at 120° C. for 60 minutes. The cured layer forms the overcoat layer having a thickness of about 4.5 µm as measured by an eddy current tester.

Photoconductor drums Prepared in Example 1 and Comparative Example 1 were installed in an electrophotographic image forming device. The electrophotographic image forming device was then operated at 50 ppm in a four-page and pause run mode. After 40 k prints, the test was stopped and the overcoat thickness loss was determined using an eddy current tester. The initial overcoat thickness (µm), image quality throughout the test, and maximum overcoat thickness loss (µm) after 40 k prints are summarized in Table 1.

TABLE 1

| Example | Overcoat Thickness (µm) | Image Quality | Max. Overcoat Thickness Loss (µm) (After 40k Prints) |
|---|---|---|---|
| Example 1 | 4.3 | Excellent | 0.3 |
| Comparative Example 1 | 4.5 | Excellent | 2.2 |

The overcoat thickness loss from the overcoat of Example 1 is dramatically lower than that of Comparative Example 1. Without wishing to be bound by theory, the inventors believe that there are at least three reasons for the improved abrasion resistance imparted by the crosslinkable charge transport molecule containing four functional groups of the present invention. (1) The presence of four acrylate groups, or more generally, four radical polymerizable functional groups, increases the crosslink density relative to a charge transport molecule with only two radical polymerizable functional groups. (2) The ethyl acrylate groups in the crosslinkable are arrayed such that the groups bonded to the 9-position of the fluorene are perpendicular to the groups bonded to the para position of the two phenyl rings. The inventors believe that this orientation further improves the 3-dimensional crosslinking imparted by the four radical polymerizable functional groups. (3) The spacer group separating the acrylates from the fluorene group and the phenyl groups is an ethyl group. The spacer group separating the acrylate from the phenyl group in Comparative Example 1 is a propyl group. The ethyl group allows for still greater crosslink density versus the propyl group by simply removing a methylene fragment.

The foregoing description illustrates various aspects of the present disclosure. It is not intended to be exhaustive. Rather, it is chosen to illustrate the principles of the present disclosure and its practical application to enable one of ordinary skill in the art to utilize the present disclosure, including its various modifications that naturally follow. All modifications and variations are contemplated within the scope of the present disclosure as determined by the appended claims. Relatively apparent modifications include combining one or more features of various embodiments with features of other embodiments.

What is claimed is:

1. A method of preparing a photoconductor comprising:
providing an electrically conductive substrate;
preparing a charge generation layer dispersion;
coating the charge generation layer dispersion onto the electrically conductive substrate to form a charge generation layer;
preparing a charge transport layer dispersion;
coating the charge transport layer dispersion over the charge generation layer to form a charge transport layer;
preparing an overcoat layer including:
an organic solvent;
about 20 to about 80 percent by weight of a charge transport molecule containing four radical polymerizable functional groups as shown below:

where $R_1$ and $R_2$ contain a spacer group and a radical polymerizable functional group, $R_3$ and $R_4$ are a non-radical polymerizable functional group, and $R_5$ and $R_6$ contain a spacer group and a radical polymerizable functional group, wherein the spacer group of $R_1$, $R_2$, $R_5$ and $R_6$ is an ethyl group and the radical polymerizable functional group of $R_1$, $R_2$, $R_5$ and $R_6$ is an acrylate group; and about 20 to about 80 percent by weight of a curing agent having a urethane containing six radical polymerizable functional groups,
coating the overcoat layer formulation over the charge transport layer; and
curing the overcoat layer formulation to form a photoconductor having an overcoat layer over the charge transport layer and the charge generation layers.

2. The method of claim 1 wherein the urethane having six radical polymerizable functional groups is a hexa-functional aliphatic urethane acrylate having the following structure:

3. The method of claim 1 wherein the overcoat layer is cured by an electron beam.

4. The method of claim 3 wherein the cured overcoat layer has a thickness of about 0.1 μm to about 10 μm.

5. A method of preparing a photoconductor comprising:
providing an electrically conductive substrate;
preparing a charge generation layer dispersion;
coating the charge generation layer dispersion onto the electrically conductive substrate to form a charge generation layer;
preparing a charge transport layer dispersion;
coating the charge transport layer dispersion over the charge generation layer to form a charge transport layer;
preparing an overcoat layer including:
an organic solvent;
a curable composition including a charge transport molecule containing four radical polymerizable functional groups as shown below:

where $R_1$ and $R_2$ contain a spacer group and a radical polymerizable functional group, $R_3$ and $R_4$ are a non-radical polymerizable functional group, and $R_5$ and $R_6$ contain a spacer group and a radical polymerizable functional group wherein the spacer group of $R_1$, $R_2$, $R_5$ and $R_6$ is an ethyl group and the radical polymerizable functional group of $R_1$, $R_2$, $R_5$ and $R_6$ is an acrylate group;

coating the overcoat layer formulation over the charge transport layer; and curing the overcoat layer formulation to form a photoconductor having an overcoat layer over the charge transport layer and the charge generation layers.

6. The method of claim 5 wherein the overcoat layer is cured by electron beam.

7. The method of claim 6 wherein the cured overcoat layer has a thickness of about 0.1 μm to about 10 μm.

* * * * *